(12) United States Patent
Eaton et al.

(10) Patent No.: US 9,324,535 B2
(45) Date of Patent: Apr. 26, 2016

(54) SELF CONTAINED IRRADIATION SYSTEM USING FLAT PANEL X-RAY SOURCES

(75) Inventors: Mark Eaton, Austin, TX (US); Mitali More, Austin, TX (US); Mike Olla, Austin, TX (US)

(73) Assignee: Stellarray, Incorporaated, Austin, TX (US)

( * ) Notice: Subject to any disclaimer, the term of this patent is extended or adjusted under 35 U.S.C. 154(b) by 420 days.

(21) Appl. No.: 12/692,472

(22) Filed: Jan. 22, 2010

(65) Prior Publication Data

US 2010/0189221 A1    Jul. 29, 2010

Related U.S. Application Data

(63) Continuation-in-part of application No. 12/201,741, filed on Aug. 29, 2008, which is a continuation of application No. 11/355,692, filed on Feb. 16, 2006, now abandoned.

(60) Provisional application No. 61/249,087, filed on Oct. 6, 2009, provisional application No. 61/249,086, filed on Oct. 6, 2009.

(51) Int. Cl.
  *G21K 5/00* (2006.01)
  *H01J 35/06* (2006.01)
  *A61L 2/08* (2006.01)
  *G21K 1/02* (2006.01)
  (Continued)

(52) U.S. Cl.
  CPC .............. *H01J 35/065* (2013.01); *A61L 2/082* (2013.01); *G21K 1/025* (2013.01); *G21K 5/02* (2013.01); *H01J 35/06* (2013.01); *H01J 35/08* (2013.01); *H01J 35/14* (2013.01); *H01J 35/16* (2013.01); *H01J 35/18* (2013.01); *A61L 2202/14* (2013.01); *A61L 2202/22* (2013.01); *A61L 2202/23* (2013.01); *A61L 2202/24* (2013.01); *H01J 2235/068* (2013.01); *H01J 2235/081* (2013.01); *H01J 2235/086* (2013.01); *H01J 2235/087* (2013.01); *H01J 2235/163* (2013.01); *H01J 2235/18* (2013.01)

(58) Field of Classification Search
  CPC ............. G21K 5/00; G21K 5/02; G21K 5/04; B01J 19/125; G21F 5/02; A61B 6/0457; A61B 6/107; A61L 2/00; A61L 2/0005; A61L 2/0041; A61L 2/082; H01J 35/16; H01J 2235/068; H01J 2235/062; H01J 2235/086; H05G 1/04; H05G 1/06
  USPC ............... 378/64, 66, 68, 119, 121–124, 134, 378/143, 195, 203
  See application file for complete search history.

(56) References Cited

U.S. PATENT DOCUMENTS

| 4,789,997 A | 12/1988 | Madsen et al. |
| 4,865,245 A | 9/1989 | Schulte et al. |

(Continued)

*Primary Examiner* — Jurie Yun

(57) ABSTRACT

The present disclosure describes a self-contained irradiator comprising at least one X-ray source inside a shielded enclosure, the one or more sources each operable to emit X-ray flux across an area substantially equal to the proximate facing surface area of material placed inside the enclosure to be irradiated. The irradiator may have multiple flat panel X-ray sources disposed, designed or operated so as to provide uniform flux to the material being irradiated. The advantages of the irradiator of the present disclosure include compactness, uniform flux doses, simplified thermal management, efficient shielding and safety, the ability to operate at high power levels for sustained periods and high throughput.

14 Claims, 10 Drawing Sheets

(51) Int. Cl.
  *G21K 5/02*   (2006.01)
  *H01J 35/08*  (2006.01)
  *H01J 35/14*  (2006.01)
  *H01J 35/16*  (2006.01)
  *H01J 35/18*  (2006.01)

(56) References Cited

U.S. PATENT DOCUMENTS

| | | |
|---|---|---|
| 5,191,517 A | 3/1993 | Stephenson |
| 5,568,021 A | 10/1996 | Bederka et al. |
| 6,333,968 B1 | 12/2001 | Whitlock et al. |
| 6,553,096 B1 | 4/2003 | Zhou et al. |
| 6,658,088 B2 | 12/2003 | Tiren |
| 6,765,987 B2 * | 7/2004 | Fleming et al. ............... 378/122 |
| 7,072,439 B2 | 7/2006 | Radley et al. |
| 7,300,634 B2 | 11/2007 | Yaniv et al. |
| 7,352,846 B2 * | 4/2008 | Kuribayashi et al. ......... 378/136 |
| 7,447,298 B2 * | 11/2008 | Busta et al. ................... 378/122 |
| 8,155,273 B2 * | 4/2012 | Eaton et al. .................... 378/136 |
| 2004/0067604 A1 | 4/2004 | Ouellet et al. |
| 2006/0273710 A1 | 12/2006 | Marking et al. |
| 2007/0237296 A1 * | 10/2007 | Wyatt et al. ..................... 378/64 |

* cited by examiner

US 9,324,535 B2

SELF CONTAINED IRRADIATION SYSTEM USING FLAT PANEL X-RAY SOURCES

REFERENCES TO RELATED APPLICATIONS

The present U.S. Utility patent application claims priority pursuant to 35 U.S.C. §120, as a continuation-in-part (CIP), to the following U.S. Utility patent application which is hereby incorporated herein by reference in its entirety and made part of the present U.S. Utility Patent Application for all purposes:

1. U.S. Utility application Ser. No. 12/201,741, entitled "FLAT PANEL X-RAY SOURCE," filed Aug. 29, 2008, issued as U.S. Pat. No. 8,155,273 on Apr. 10, 2012, which claims priority pursuant to 35 U.S.C. §120 as a continuation to the following U.S. patent application which is hereby incorporated herein by reference in its entirety and made part of the present U.S. Utility Patent Application for all purposes:

a. U.S. Utility application Ser. No. 11/355,692, entitled "COMPACT RADIATION SOURCE," filed Feb. 16, 2006.

The present U.S. Utility patent application also claims priority pursuant to 35 U.S.C. §119(e) to the following U.S. Provisional Patent Application which is hereby incorporated herein by reference in its entirety and made part of the present U.S. Utility patent application for all purposes:

1. U.S. Provisional Application Ser. No. 61/249,086, entitled "SELF CONTAINED IRRADIATION SYSTEM USING FLAT PANEL X-RAY SOURCES," filed Oct. 6, 2009.

2. U.S. Provisional Application Ser. No. 61/249,087, entitled "PANORAMIC IRRADIATION SYSTEM USING FLAT PANEL X-RAY SOURCES," filed Oct. 6, 2009.

STATEMENT REGARDING FEDERALLY FUNDED RESEARCH AND DEVELOPMENT

This invention was made with Government support under Contract No. 70NANB7H7030 awarded by the Advanced Technology Program of the National Institute of Standards and Technology. The U.S. Government has certain rights in the invention.

TECHNICAL FIELD OF THE INVENTION

The present disclosure relates generally to an irradiation system and method, and more particularly, to a self-contained X-ray irradiator system and method wherein the X-ray flux generation area of a source is substantially equal to the proximate target surface area.

BACKGROUND OF THE INVENTION

Ionizing radiation, such as electron beams, gamma rays and X-rays, is widely used for the irradiation treatment of objects, including: the sterilization of medical, pharmaceutical, food and cosmetic products; the cross-linking of polymers and other industrial processes; the inactivation of leukocytes in transfusion blood supplies; the sterilization of insects for phytosanitary and research purposes; the attenuation of organism function for vaccine development, and many other purposes.

Broadly speaking, irradiators are classified as either self-contained irradiators or panoramic irradiators. In self-contained irradiators, the radiation source, radiation shielding, the objects to be treated, any systems for the movement of those objects, and sometimes the power supply, are all in one enclosure. X-ray versions are regulated by the U.S. Food and Drug Administration under the category "X-ray cabinet irradiator" (Title 21 CFR §1020.40). Panoramic irradiators are generally larger than the self-contained irradiators and use a material transport system to move the objects to be treated from an area where people may safely operate to a separately-shielded irradiation area receiving flux from the radiation source.

The radiation source used in either type of irradiator may include: gamma rays emitted by the decay of radioactive isotopes; electron beams produced by linear accelerators, electron tubes or other methods; or X-rays produced by the impact of high energy electrons upon a metal target, for example in an X-ray tube.

The predominant radiation sources for self-contained irradiators are radioactive isotopes and X-ray tubes. Radioactive isotope irradiators comprise: a sealed isotope source, most commonly Cesium-137 but in some cases Cobalt-60 [US NRC 2007]; a massive lead enclosure for this source, the lead commonly weighing over a ton; a vessel to hold the objects to be treated; and an internal transportation system to move this vessel from a cabinet section, where an operator may safely load and unload this vessel, to the lead-shielded radiation treatment section, all of these components being contained in one overall enclosure. The radioactive isotope constantly emits radiation due to natural radioactive decay. The isotope sources produce highly energetic gamma rays in the high keV (662 keV for Cs-137) to MeV (1.25 MeV for Co-60) range. The higher energy Co-60 sources require twice as much lead shielding as the Cs-137 sources, and also have a shorter half life, so Cs-137 has been the preferred source and was being used in most of the 1,341 isotope-based self-contained irradiators in the United States in 2007 [US NRC 2007].

About half of all isotope-based self-contained irradiators are used for blood irradiation and the remaining half for other purposes, including medical, scientific and agricultural research [US NRC 2007]. Blood is routinely irradiated at blood banks and hospitals to prevent the development of transfusion associated graft-versus-host disease (TA-GVHD) in immuno-suppressed patients. TA-GVHD is a usually fatal condition in which viable leukocytes in the transfused blood attack recipient organs and tissues. Irradiation renders the leukocytes unviable and is currently the only recommended method for GVHD prevention [BCSH Blood Transfusion Task Force]. Current guidance from the Food and Drug Administration (FDA) recommends a dose of 25 Gy delivered to the mid-plane of the blood container with no part of the blood container to receive less than 15 Gy. Most blood irradiators units in use today are self-contained, isotope-based systems using Cs-137. Many of the self-contained irradiators used in research also employ Cs-137 or Co-60. These typically deliver dose rates of 1-10 Gy/min to a cavity of 4 to 10 liters in size. These higher doses necessitate heavier shielding, so these units are larger and often weigh three or four tons. Even the smaller Cs-137 units take up valuable floor space at blood banks and hospitals and are cumbersome to operate.

The isotopes used in these irradiators could also be used in a radioactive dispersal device ("dirty bomb") and have therefore become a major public security concern. Cs-137 and Co-60 account for nearly all (over 99 percent) of the sealed sources that pose the highest security risks in the United States [US NRC 2007]. Cs-137 is of particular concern since it is made in powder form and is therefore easily dispersible, because it has a relatively long half-life, and because it is present in major population centers. The primary use of Cs-137 is in self-contained irradiators for blood and research purposes. The National Research Council of the National Academy of Sciences' Committee on Radiation Source Use and Replacement identified Cs-137 as the top priority for the development of replacement technologies. Security concerns have added substantially to the acquisition and operating costs of irradiators using Cs-137.

Self-contained or cabinet irradiators using X-ray sources, such as those made by Faxitron X-Ray LLC, have found use in many applications, though generally not those now served by isotope irradiators. Most prior art X-ray irradiators use a single X-ray tube as the radiation flux source.

FIG. 1 shows the general architecture of prior art X-ray tubes. X-ray tubes are point sources of radiation, as shown in FIG. 1, wherein X-rays are generated by the impact of a high voltage electron beam 50 from a heated filament or other cathode 10 at a point (sometimes called the spot) on a metal anode 30, typically disposed at an angle relative to the cathode so as to allow X-ray flux 60 to exit one side of the vacuum tube enclosing the cathode and anode. This entire side may comprise the flux exit window of the tube, or a separate window 20 of a low Z material such as beryllium may be built into this side of the tube or housing for the tube. In tubes operating below cathode to anode voltages of 150 KV, less than 2% of the energy from the electrons is converted into X-rays, while the rest is dissipated as heat on the anode.

Though X-rays have long been known as a possible substitute radiation source for many of the uses of isotope-based self-contained irradiators, including blood irradiation [Janatpour 2005], several limitations of prior art X-ray irradiators have prevented their adoption. Irradiators using an X-ray tube will deliver an uneven dose to the irradiation target, for example a blood bag, since the X-rays will first impinge on one surface of the target and then be attenuated as they pass through the target material. X-rays from a single point on the anode will be emitted in all directions. Those which go back into the target will not be useful for irradiation, but will instead generate heat. With the X-ray target angled as shown in FIG. 1, even more of the X-rays are absorbed in the target than would be the case with a target disposed normal to the axis of the electron beam, a phenomenon known as the heel effect. Irradiation efficiency is further reduced by the fact that, of those X-rays directed away from the target, only those which impinge on the irradiation target surface will do useful work; the rest are absorbed by shielding structures. At the same time, the target surface area, to be useful in most irradiation applications, must be many times larger than the spot on the anode of an X-ray tube. As the intensity of the X-ray flux is inversely related to the square of the separation, the tube output has to be increased to meet the irradiation needs.

FIG. 2 shows the throw distance needed for prior art point sources used in irradiation. The cabinet and shielding must also be enlarged to accommodate the throw distance 200 shown in FIG. 2 that is required to cover a target area 400 with length and width 410. Furthermore, since all the flux needed for the application must come from one spot on the anode, there is a tremendous thermal load on this small area, which in turn necessitates the use of complex liquid cooling systems for higher flux applications.

Some recent inventions have taught the use of two or more X-ray tubes in a cabinet blood irradiator, such as U.S. Pat. Nos. 6,212,255 and 6,614,876. The X-ray tubes have been high-power models, with anode voltages of 160 kV, designed for applications such as computed tomography systems. While some aspects of an X-ray blood irradiator can be improved by using multiple tubes, rotating canisters are still needed to provide a uniform dose to the blood products, and the irradiator cabinet and shielding must be essentially twice as large to accommodate the flux throw distance from two tubes. Even with more than one tube, the use of a point source of X-rays still places a tremendous heat load on one spot, so externally-connected liquid cooling systems are still needed. In practice, these have proven to be cumbersome and unreliable, thereby limiting the adoption of X-ray systems for blood irradiation [Dodd, 2009].

More recently, a new type of specimen and blood irradiator consisting of a center-filament X-ray tube that irradiates 360 degrees around the tube and a cylindrical gold target has been described in U.S. Pat. No. 7,346,147. The electron source is a thermal cathode in the form of an elongated filament mounted along the axis of the cylindrically shaped transmissive type anode. Instead of a point source as is the case in most X-ray tubes, this invention is in the form of a line source. The electrons impinge on the interior surface of the anode and the X-rays generated penetrate the anode material and exit out of the exterior surface of the anode. The anode has to be made very thin (14 micron Au on 4 mil Al) in order to generate the forward directed X-rays. Flat panel versions of this kind of source using a transmissive anode are disclosed in U.S. Pat. Nos. 6,477,233 and 6,674,837. Two major limitations of this kind of source are the thermal loading capacity of the thin-film anode, and the thermal matching of the anode to the exit window of the source. Even with externally-connected liquid cooling systems, only limited amounts of X-ray power can be obtained from this kind of source. The X-ray irradiation apparatus taught by Avnery in U.S. Pat. Nos. 6,738,451, 7,133,493, and 7,324,630 also uses X-ray sources relying on a transmissive anode/X-ray target and thus having these same limitations.

Another X-ray source had been disclosed in U.S. Pat. No. 7,447,298 having a thermionic or cold cathode array inside a vacuum enclosure, which can direct e-beam current to a thin film X-ray target disposed on an exit window located above the cathode array with reference to the direction of the e-bam and X-ray fluxes, or, with a second cathode array, to a wide area anode located below the first cathode array, the second cathode arrays and the exit window with the thin-film anode. This source will have the heat dissipation limitations as discussed above for the thin-film X-ray target. X-rays produced by the lower, "reflective" anode will be attenuated first by the cathode arrays and their support structures, and then the thin-film X-ray target, resulting in an inefficient system. The second anode, while it can be thicker and have higher heat dissipation capacity than a thin-film anode, is inside the vacuum enclosure. The heat must therefore be transferred through the vacuum enclosure, which will limit the amount of X-ray flux that can be achieved with this source.

BRIEF SUMMARY OF THE INVENTION

Embodiments of the present disclosure are directed to systems and methods that are further described in the following description and claims. Advantages and features of embodiments of the present disclosure may become apparent from the description, accompanying drawings and claims.

Embodiments of the present disclosure provide an irradiation system and method wherein the X-ray flux generation area of a substantially planar source is substantially equal to the proximate target surface area facing X-ray flux generation area. The system utilizes a flat panel X-ray source, which generates high intensity X-ray flux over a large area. As this X-ray flux generation area is substantially planar, the X-ray flux remains substantially uniform within the irradiation chamber. One or more flat panel X-ray sources are placed around the irradiation chamber to generate X-ray flux. The design of the present disclosure provides a compact, efficient and safe irradiation system.

Embodiments of the present disclosure provide a compact, safe and highly efficient self-contained X-ray irradiation system that offers significant advantages over prior art approaches. More specifically, the present disclosure provides a compact system for X-ray irradiation wherein the X-ray flux generation area of a source is substantially equal to the proximate facing surface area of the material to be irradiated. The irradiator includes at least one flat panel X-ray source which generates a wide source of X-ray flux. One or more flat panel X-ray sources are disposed between the irradiator enclosure and the area in which the irradiation takes place, so that the X-ray flux is directed inward towards the material to be irradiated. The flux exit windows of the sources face the material to be irradiated and the anode targets sources face the irradiator enclosure. Much of the X-ray flux which passes by or through the material being irradiated will be absorbed by the anode target of an opposite flat panel X-ray source, providing a degree of self-shielding and reducing the need for other shielding materials. Since the X-ray sources are wide, and the flux generation area is substantially equal to the irradiation target area, minimal throw distance is needed compared with a point source, which allows the irradiator to be made yet more compact.

According to one embodiment of the present disclosure an apparatus and method for the X-ray irradiation of materials. This apparatus includes an irradiation chamber, a number of flat electromagnetic (X-ray) sources, a support mechanism, a heat transfer system, and a shielding system. A shielded portal within the shielding system allows access to an interior volume of the irradiation chamber. The shielded portal allows materials to be placed in and withdrawn from the irradiation chamber. When closed, the shielded portal allows a continuous shielded boundary of the interior volume of the irradiation chamber. The electromagnetic sources are positioned on or embedded with interior surfaces of the irradiation chamber. These electromagnetic sources may generate an electromagnetic flux, such as an X-ray flux, where this flux is used to irradiate the interior volume of the irradiation chamber and any materials placed therein. The materials placed within the interior of the chamber may be supported by a low attenuation support mechanism. This low attenuation support mechanism does not substantially reduce the X-ray flux intended to irradiate the materials placed within the interior volume of the irradiation chamber. Additionally the irradiation chamber may have a heat transfer system thermally coupled to the irradiation chamber and electromagnetic sources in order to remove heat from the interior surfaces of the irradiation chamber. The shielding system external to the irradiation chamber prevents unwanted radiation from escaping from within the irradiation chamber.

Another embodiment of the present disclosure provides a method for the X-ray irradiation of materials. This method involves transporting a work piece or material to be irradiated to an irradiation chamber. The work piece or materials are placed within the irradiation chamber and supported with a mechanism such as a low attenuation support mechanism. This low attenuation support mechanism does not substantially reduce the electromagnetic flux (X-ray) flux within the irradiation chamber. One or more flat electromagnetic (X-ray) sources may be energized to irradiate the interior volume of the irradiation chamber. This allows the work piece or materials to be irradiated within the chamber. Excess heat may be removed with a heat transfer system in order to prevent the irradiation chamber/electromagnetic source from overheating. Additionally the irradiation chamber may be shielded to prevent the irradiation of objects and materials external to the irradiation chamber.

Yet another embodiment of the present disclosure provides another system for the X-ray irradiation of materials. This system includes an irradiation chamber, a number of flat X-ray sources, a transport mechanism, a low attenuation support mechanism, a heat transfer system, a shielding system, and a process controller. The irradiation chamber has an inner volume wherein the flat X-ray sources are positioned within or on the interior surfaces of the irradiation chamber such that the flat X-ray sources may irradiate the interior volume of the irradiation chamber. The transport mechanism allows materials to travel to and from the irradiation chamber. Within the irradiation chamber the low attenuation support mechanism supports the work pieces or materials to be irradiated while not substantially reducing the X-ray flux available for the irradiation of these objects. The heat transfer system removes heat from the X-ray source and the shielding system external to the irradiation chamber prevents inadvertent irradiation of materials and objects outside the irradiation chamber. The process controller coordinates the operation of the irradiation chamber, X-ray source, heat transfer system and an interlock system which prevents irradiation while access to the interior volume is open.

BRIEF DESCRIPTION OF THE SEVERAL VIEWS OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION OF THE INVENTION

Preferred embodiments of the present disclosure are illustrated in the FIGs., like numerals being used to refer to like and corresponding parts of the various drawings.

Embodiments of the present disclosure provide an apparatus and method for the X-ray irradiation of materials. This apparatus includes an irradiation chamber, a number of flat electromagnetic (X-ray) sources, a support mechanism, a heat transfer system, and a shielding system. A shielded portal within the shielding system allows access to an interior volume of the irradiation chamber. The shielded portal allows materials to be placed in and withdrawn from the irradiation chamber. When closed, the shielded portal allows a continuous shielded boundary of the interior volume of the irradiation chamber. The electromagnetic sources are positioned on or embedded within interior surfaces of the irradiation chamber. These electromagnetic sources may generate an electromagnetic flux, such as an X-ray flux, where this flux is used to irradiate the interior volume of the irradiation chamber and any materials placed therein. The materials placed within the interior of the chamber may be supported by a low attenuation support mechanism. This low attenuation support mechanism does not substantially reduce the X-ray flux intended to irradiate the materials placed within the interior volume of the irradiation chamber. Additionally the irradiation chamber may have a heat transfer system thermally coupled to the irradiation chamber and electromagnetic sources in order to remove heat from the interior surfaces of the irradiation chamber. The shielding system external to the irradiation chamber prevents unwanted radiation from escaping from within the irradiation chamber.

Embodiments of the present disclosure improve upon prior art self-contained irradiators through the use of one or more flat-panel, broad-area X-ray sources capable of delivering more substantial flux dose rates in a format well-suited to efficient irradiation. The most general aspect of the present disclosure is the generation of the X-ray flux in the self-contained irradiator from a broad area anode, including a broad area anode that can be easily cooled to dissipate the heat produced in X-ray generation.

Figure 1:
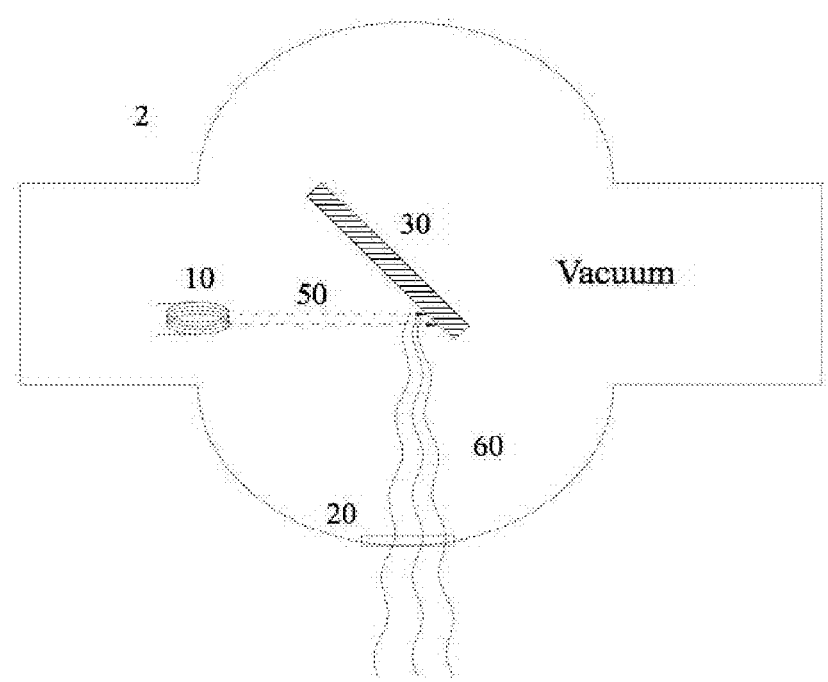
FIG. 1 shows the general architecture of prior art X-ray tubes.
Figure 2:
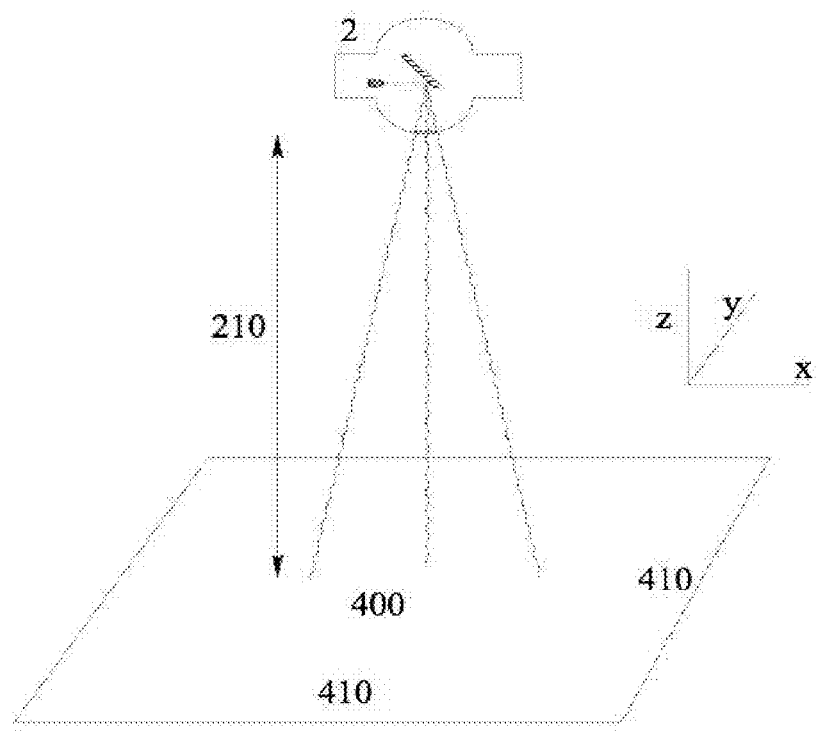
FIG. 2 shows the throw distance needed for prior art point sources used in irradiation.
Figure 3:
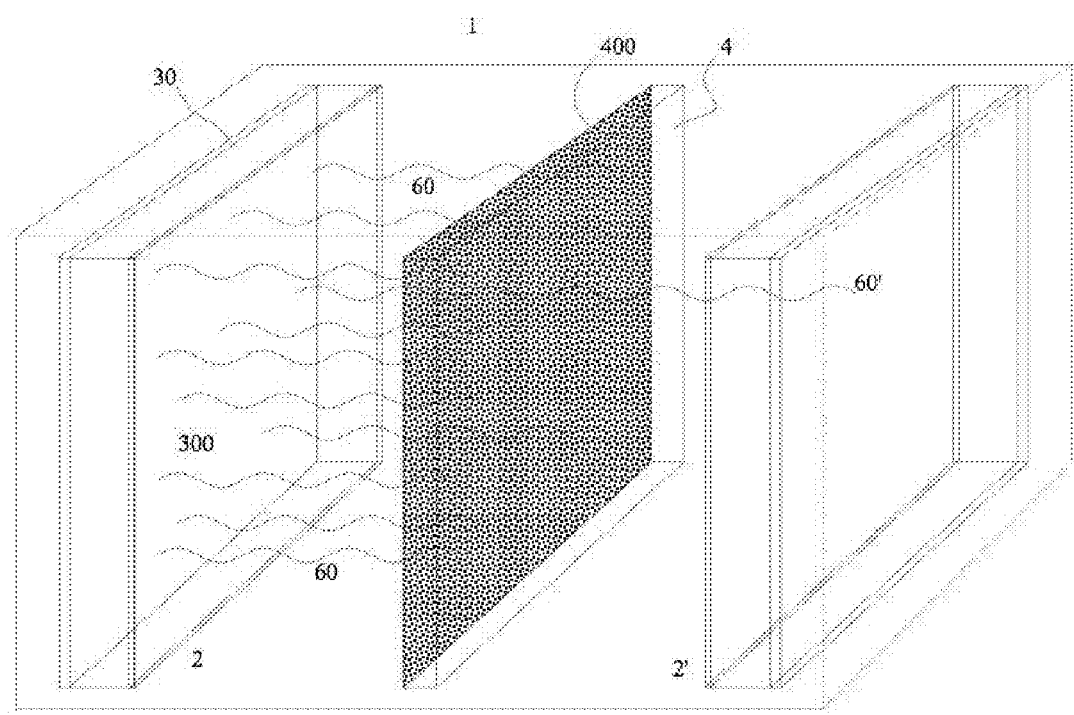
FIG. 3 is a diagram of the general architecture of the irradiator with the flux generation area of a source substantially equal to the proximate facing surface area of the material being irradiated in accordance with embodiments of the present disclosure.

FIG. 3 is a diagram of the general architecture of the irradiator with the flux generation area of a source substantially equal to the proximate facing surface area of the material being irradiated in accordance with embodiments of the present disclosure. In self-contained irradiator 1, the flux generation area 300 on the surface of wide, flat anode 30 of a flat panel X-ray source is substantially equal to the proximate facing surface area 400 of the material to be irradiated 4, both of which are enclosed in cabinet 5 of the irradiator. Flat panel X-ray source 2 may be made in any area format, for example, circular, rectangular or square, and in sizes ranging from a few square centimeters to a square meter or more. Since flux generation area 300 and irradiation target area 400 are substantially the same, no extra throw distance is needed in the z-axis, so the X-ray sources may be placed in close proximity to the irradiation target material, allowing the irradiator to be made compact.

Among the many materials that can be irradiated with this disclosure are blood bags of transfusion blood supplies, medical or surgical implants, general hospital materials, vaccine and other cultures, samples of food or cosmetics, insects, or materials for research purposes. Some items may be irradiated directly, while others, such as fluids, will be irradiated inside a container penetrable by X-ray flux. The present disclosure is well-suited for the irradiation of materials with contoured or irregular surfaces, since X-ray flux is emitted at all angles at a multitude of locations across source anode surface 300, allowing the flux to hit the target surface from many different directions, and since source 2 may be operated at high voltage and high power to generate X-rays with high penetrating ability.

In the case of fluids such as blood in a blood bag, it is advantageous to orient the X-ray source 2 horizontally, above or below the material, so that bag 4' can lay flat and the blood can be evenly distributed. FIG. 3 also shows the use of two flat panel X-ray sources, with source 2 above and source 2' below target material 4, which provides for more even distribution of X-ray flux through the material in the z direction. A rack, frame or tray is used inside irradiator 1 to support material 4. A rotational means may also be provided inside irradiator 1 to help ensure even distribution of the X-ray flux inside material 4. Tubes or other fluid flow channels may also be used inside the chamber. In other aspects of the disclosure, the sources may be oriented vertically and placed on the sides of the irradiator, or sources may be placed on all sides of the irradiator, as well as the top and bottom. The cubical irradiator shown in FIG. 3 is an exemplary design; irradiator 1 may be made in circular, hexagonal, octagonal or other shapes. Flat panel X-ray sources 2 may also be designed or operated to produce different power levels or X-ray energy distributions to suit a particular application. A collimating grid may be placed in front of flat panel X-ray source 2, so as to allow the source to be used for imaging applications, with film or other X-ray detector means placed on the opposite side of material 4 from source 2.

An important advantage of multiple sources as used in the present disclosure is self shielding. Sources 2 can be operated with electrical current and anode potential calibrated to deliver as much of the generated X-ray flux as possible into the material to be irradiated. As depicted in FIG. 3, however, some of the X-rays 60' will pass through the material and exit the opposite side. These X-rays will then be absorbed, primarily by the anode of the opposite source 2', thereby reducing the need for additional shielding material in the irradiator. With more than two sources, for instance four sources in two opposing pairs, even more of the unused flux will be absorbed through self-shielding.

Figure 4:
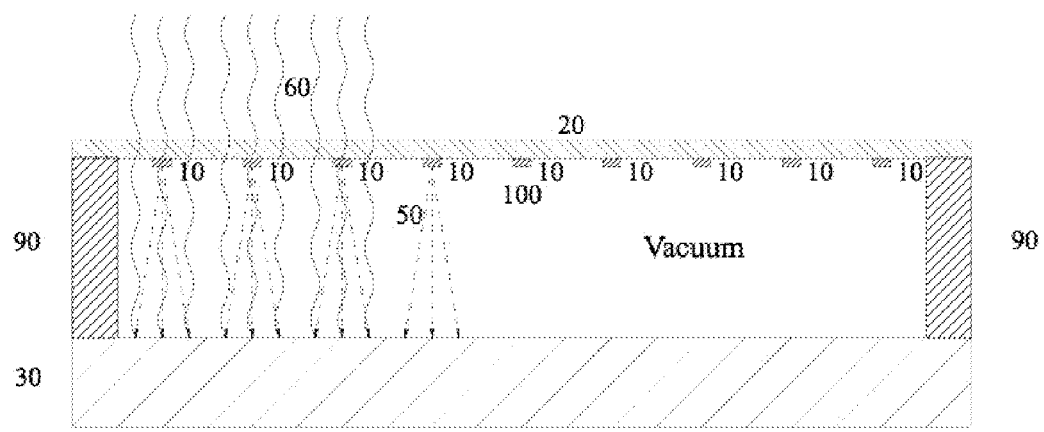
FIG. 4 is another diagram of the general architecture of flat panel X-ray sources in accordance with embodiments of the present disclosure.

FIG. 4 is another diagram of the general architecture of flat panel X-ray sources in accordance with embodiments of the present disclosure. Detail as to a type of flat panel X-ray source which can be used in the irradiator of this disclosure is shown in FIG. 4. Source 2, the preferred flat X-ray source of this disclosure has an array 100 of cathodes 10 on exit window 20 of the source, with open space between the cathodes in the array so as to provide a wide area source of electrons. A wide, flat metallic X-ray target 30 is disposed opposite cathode array 100, the target having one major surface facing cathode array 100 and exposed to the vacuum of the source and the other major surface exposed to the exterior of the source. Exit window 20 and X-ray target 30 are the integral major parts of the vacuum enclosure of the source, with side walls 90 completing the vacuum enclosure. Cathode array 100 is operable to emit multiple electron beams 50 towards X-ray target 30 to generate X-ray flux 60, a portion of which will be emitted in the direction of cathode array 100 and pass through or by this array and out through exit window 20, and on to the material to be irradiated.

Exit window 20 of X-ray source 2 can be made of several different materials, including various types of glass, sapphire, ceramic, plastic that has been passivated for operation in vacuum, various forms of carbon sheet, beryllium and boron carbide. In general it is desirable for window 20 to be made of materials with a low atomic number Z and to be as thin as possible consistent with structural integrity under vacuum load, so as to allow as much of the X-ray flux as possible to pass through and be used for irradiation. Side walls 90 of the source can be made of the same materials as exit window 20. In general it is desirable to use the same materials for these parts of the source, or else materials that have a close match of thermal expansion, since heat from anode 30 propagates throughout the entire construction ands mismatched materials can cause stresses leading to vacuum leaks, rendering the source inoperable. Anode 30, which forms the X-ray target, can be made of any material, but is preferably made of a metal with a high Z number so as to increase X-ray generation. Common materials used for the anode in traditional X-ray tubes, such as tungsten, copper, molybdenum or ruthenium, can also be used for anode 30 in source 2. An exemplary materials set for these primary components of source 2 is a sapphire window, Macor or alumina side walls and an anode/target made of an 80/20 tungsten-copper alloy, all of which have a coefficient of thermal expansion in the neighborhood of $8.5$ or $9 \times 10^{-6}$ in./in.*/° C. Another exemplary materials set is soda lime glass for the window and side walls and plain tungsten for the anode, for matched coefficients of thermal expansion in the neighborhood of $4.5 \times 10^{-6}$ in./in.*/° C. over the temperature range of interest. For anode 30, a flat sheet or slab of tungsten or tungsten-copper alloy of 1 mm or more in thickness will have more than sufficient rigidity to support the atmospheric load on the package, which is pumped down to an internal pressure of $10^{-5}$ to $10^{-8}$ Torr. Sheets of 3 to 6 mm have been used in prototypes and found to have good mechanical and thermal properties. Exemplary thicknesses for the side walls are 2 to 10 mm for glass or ceramic. Exit window 20 should be as thin as possible, preferably in the range of 0.5 to 10 mm for glass or ceramic, with the thinness of the window determined in part by the unsupported span over which it must maintain structural integrity under vacuum. Internal spacers, not shown in FIG. 4, can be used to reduce this span, with the spacers made of the same materials as the side walls or exit window.

The overall thickness of flat panel X-ray source 2 is determined by the thickness of window 20, the thickness of anode 30 and the wall and spacer separation between them. This separation will be considerably larger than the window and anode thicknesses, since sufficient distance must be provided between cathode array 100 and anode plate 30 to prevent arcs both inside the vacuum envelope of source 2 and between any externally exposed cathode and anode connections. Panel source 2 is operated at an anode to cathode voltage between 10 kV and 250 KV, with 80-120 KV being an exemplary range for transfusion blood irradiation. In the 100 KV range for blood irradiation, a separation of 2 cm between cathode array 100 and anode 30 is more than sufficient to prevent vacuum breakdown and arcing inside the package. Externally, without additional electrical insulation and using prudent safety factors to account for humid air and other factors which can lead to the development of arcs, a separation of 15 cm or more is desirable. It is advantageous therefore to attach an oil, gas, vacuum or other insulation section to the externally exposed major surface of anode 30 so as to electrically isolate the anode from external arcs. This insulation section, such as an oil pan, is also used as or as part of a cooling system for anode 30, which allows source 20 to be operated at higher power levels. Exemplary thicknesses of source 20 for operation up to 150 KV and with an insulation and cooling structure attached, are from 5 cm to 20 cm.

Cathode array 100 is formed directly on to, attached to or supported by window 20 of source 2. Array 100 may be made of either field emission cold cathodes or thermal filament cathodes. Space between the cathodes 10 of array 100 is provided to spread out the electron source generating the X-ray flux. This space can also be used for the placement of support structures for thermal filament cathodes or for resistors, buss lines and gating or extractor structures for field emission cold cathodes. Field emission cathode arrays are formed directly on window 20 using micro fabrication techniques. Alternatively, a field emission cathode array may be formed on a separate substrate which is then attached to or placed in front of flux exit window 20. Thermal filaments are stretched across the surface of window 20 and held in place by metallic, glass, ceramic or other support structures which are fused, frit sealed, welded or otherwise bonded to the window. Alternatively, a frame may be provided for the stretching and separation of thermal filament cathodes, and this frame may be attached to window 20 or placed in front of window 20 and supported by side walls 90.

In operation, the cathodes 10 in array 100 are caused to emit electrons, either through heating of the filament cathodes or through field emission extraction of current in cold cathode array. Hundreds of thousands or millions of cold cathodes can be formed into array 100, and in the case of thermal cathodes, numerous filaments can be stretched or patterned to make the array, so a very large number of electron beams will be emitted from array 100 and accelerated by the cathode to anode potential to hit anode 30, where they will generate X-rays across the surface of the anode through the classical Bremsstrahlung and characteristic line emission processes. X-ray flux in generated in all directions through these processes. About half of the generated X-rays will be emitted into anode/X-ray target 30 and serve no useful purpose. The other half will be emitted away from the anode and towards exit window 20 and the material to be irradiated, with some of the rays being absorbed by the side walls or internal spacers and some of the lower energy rays emitted in the direction of the target material being absorbed in array 100 or window 20. With a reasonably thin window 20, however, most of the X-ray flux that escapes the anode will be directed towards target material 4 and either be absorbed in the material, thereby serving the purpose of irradiation, or pass through material 4.

Figure 5:
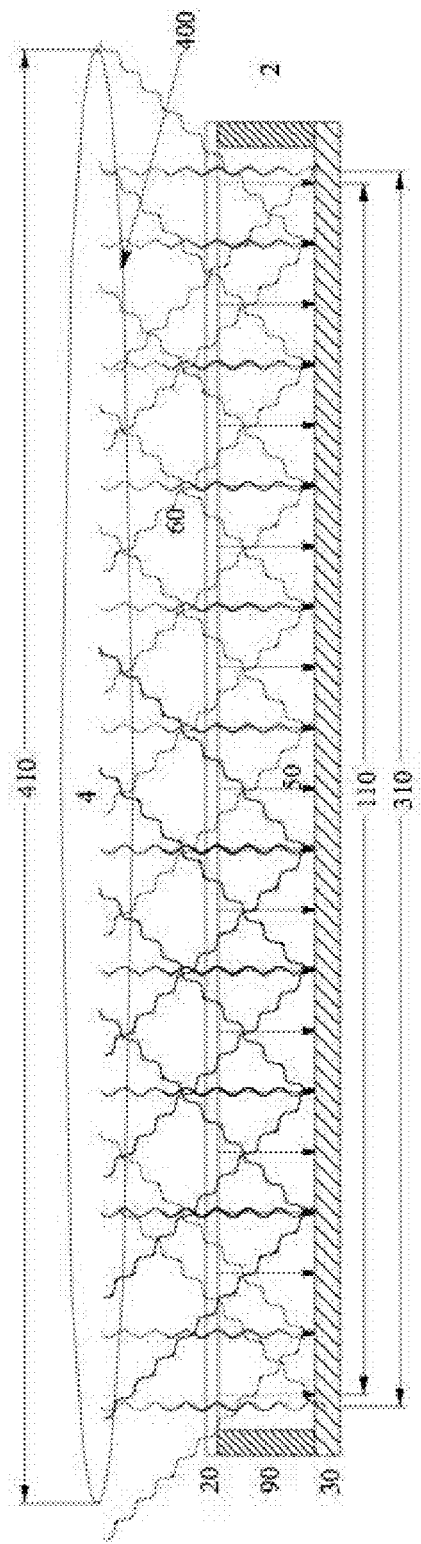
FIG. 5 is a diagram of the X-ray flux distribution from two flat panel X-ray source provided in accordance with embodiments of the present disclosure.

FIG. 5 is a diagram of the X-ray flux distribution from two flat panel X-ray source provided in accordance with embodiments of the present disclosure. This diagram shows the cross sections of the source provided in accordance with embodiments of the present disclosure and material being irradiated. Dimension 110 shows the width of the cross section of the cathode array on window 20, or by that part of array which is caused to emit electrons, while dimension 310 shows the cross sectional width of the flux generation area on anode 30 and dimension 410 shows the cross sectional width of surface 400, the proximate facing area of the material being irradiated 4. The flux generation area on anode 30, as indicated by cross sectional width 310, is essentially determined by the area of the cathode array on window 20, or by that part of array which is caused to emit electrons, as indicated by cross sectional width 110. This is because at high anode potential, and without any means of deliberately deflecting electron beams 50, these beams will head straight at anode 30 and diverge laterally by only a very small distance. Only those beams produced by cathodes at the outer perimeter of the emitting area of array 100 will fall outside of the corresponding area on the anode, and this by a very slight degree. Most of the X-rays 60 which are generated on anode 30 will in turn be directed towards the corresponding area 400, over its cross sectional width 410, on the proximate surface of the material being irradiated 4. Some of the X-rays, particularly those emitted around the perimeter of the anode, will be absorbed in the side walls, and a small percentage will be emitted at such a shallow angle as to cause them to miss irradiation target surface 400, but with a wide flux generation area, substantially all of the X-ray flux leaving anode 30 will be directed towards proximate surface 400 on the material to be irradiated.

The wide area of anode 30 provides one of the major advantages of source 2, which is relatively easy thermal management of the heat generated on the anode, since the heat can be dissipated over a broad area and the exterior side of anode 30 can be directly coupled to atmosphere, forced air, oil bath or circulating fluid heat dissipation systems.

Figure 6:
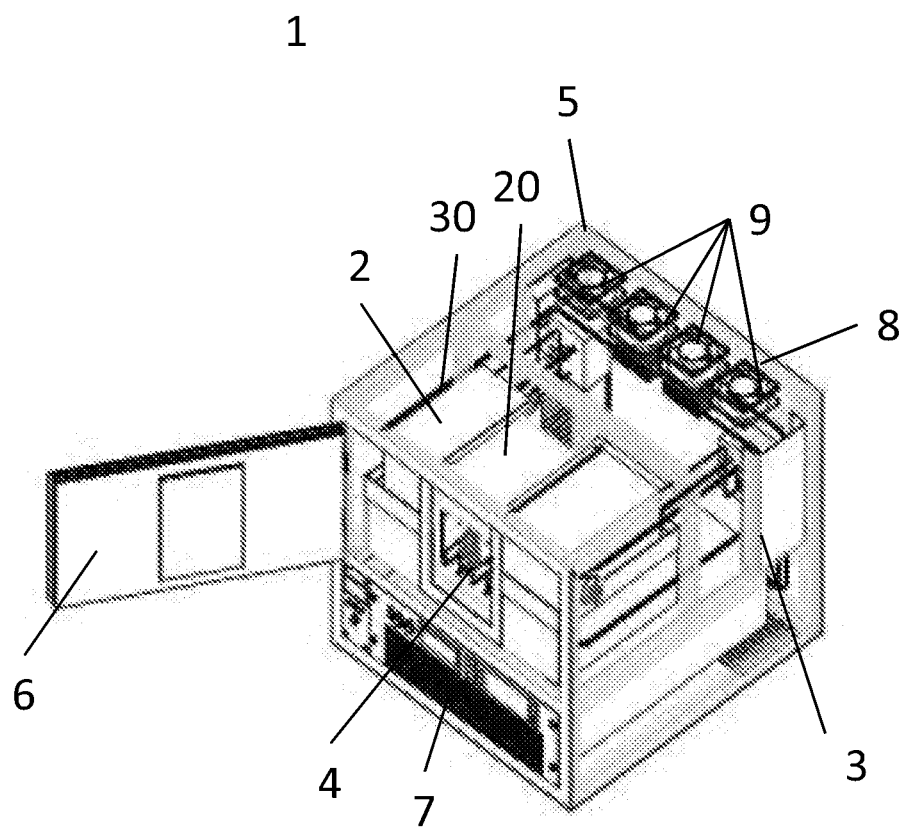
FIG. 6 is a diagram of another embodiment of an irradiator in accordance with embodiments of the present disclosure.

FIG. 6 is a diagram of another embodiment of an irradiator in accordance with embodiments of the present disclosure. Further aspects of irradiator 1 as shown are in this case with flat panel X-ray sources 2 arranged on either side of irradiator enclosure or frame 5, with anodes 30 closest to the enclosure and windows 20, with the cathode arrays, facing inwards. Material to be processed 4 is placed inside the irradiator between the panels. The material may be supported by a vertical frame or rack made out of a low Z material as carbon or Plexiglas so as to minimize attenuation of the X-ray flux. In another embodiment, a carousel can be provided to rotate the material to be irradiated for uniform distribution of dose. Power supply 7, incorporating a voltage amplifier to bring wall socket power up to the high potential needed for X-ray generation, is placed at the bottom of the cabinet and supplies power to both the X-ray panels. Optional heat exchanger system 8 for high power operation is placed at the rear of the cabinet with fans 9 for cooling. Enclosure 5 is lined with shielding material 3, such as lead sheet, to absorb any radiation which is not absorbed by material 4 or opposing anodes 30. Flat panel X-ray sources 2 may have an oil-filled casing attached to cover anodes 30 and provide high voltage insulation. The oil can be circulated through tubing to heat exchanger 8 to allow operation at high power levels. In lower power designs, the heat exchanger can be eliminated and the anode cooled simply by air drawn through the cabinet by fans 9, which can be simple muffins fans. In either case, the high voltage insulation and cooling system is entirely contained within the irradiator enclosure. Other high voltage insulation, such as plastic or ceramic sheets may be used in place of an oil casing. Thermal insulation structures may be built into the irradiator chamber or used in frames or trays to support irradiated material isolate the material from the heat generated during X-ray production. A swing door 6, also lined with shielding material, provides access to the inside of the irradiator. Interlocks and other safety features may be incorporated for safer operation. Interlocks on the door, for example, will shut off power when the door is opened. An X-ray ON light on the outside of the box may be activated when power is supplied to the X-ray sources. An emergency switch may be provided to turn off power in case of emergency. Controls are provided to set the irradiation time, current levels and voltage to the X-ray sources. A bar code scanner may also be attached to the irradiator to allow tracking of throughput. An internal radiation dose measurement system may be provided for recording the dose delivered to each lot of material irradiated.

The size of irradiator 1 is determined primarily by the size and format of the flat panel X-ray sources used. For blood irradiation, for example, square panels 30 cm on a side may be used to allow processing of four blood bags, each roughly 15 cm on a side, placed in a horizontal rack or vertical frame, so that the flux generation area of the panels is substantially equal to the proximate facing area of the blood bags. For higher throughput, two or more of these frames or racks may be placed between the flat panel X-ray sources to allow processing of 8, 12 or more bloods bags at a time.

Figure 7:
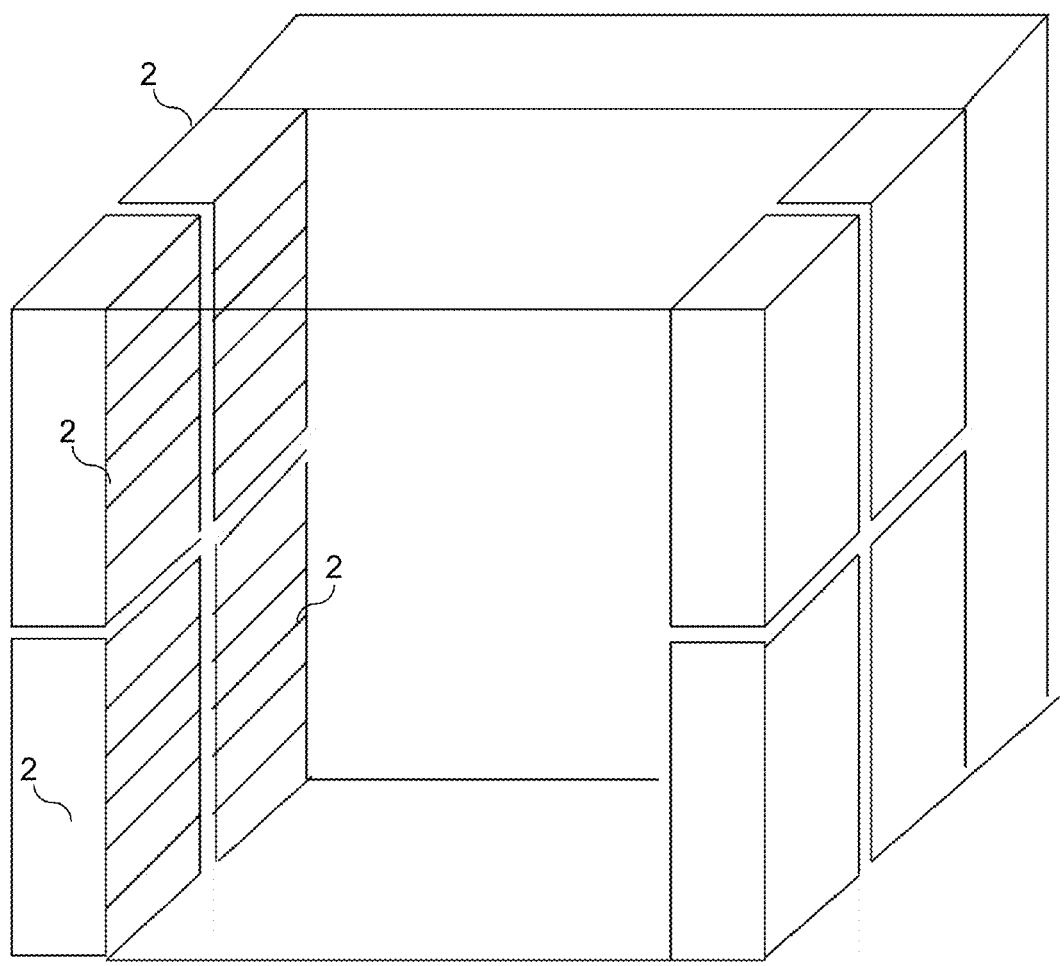
FIG. 7 is a diagram of a large volume irradiation system with multiple panels tiled where each panel can be individually addressed or all can be operated simultaneously in accordance with embodiments of the present disclosure.

FIG. 7 is a diagram of a large volume irradiation system with multiple panels tiled where each panel can be individually addressed or all can be operated simultaneously in accordance with embodiments of the present disclosure. Here, several smaller flat panel X-ray sources 2 may be tiled together to provide a larger flux generation area. For example, four square panels, each 25 cm on a side, may be arranged to provide a flux generation area of 50 cm×50 cm. Two such tiled panel configurations are shown in FIG. 7 on opposite sides of an irradiator. The panels can then be activated via the irradiator control system to deliver radiation doses matched to the material to be irradiated. For example, with material having a large proximate surface area, all four panels on each side can be activated. For material resting on the bottom of the enclosure and having a smaller proximate surface area, only the bottom two or perhaps even only one panel on each side will need to be activated for the most efficient use of power. Vertical frames or horizontal trays may be provided with areas matching the panels. Depending on where the materials, such as blood bags, are placed in these frames or trays, the operator can then determine which panels to activate. A further advantage of tiling several flat panel X-ray sources together on a side of an irradiator is redundancy, since if one panel fails the other can still be operated.

Figure 8A:
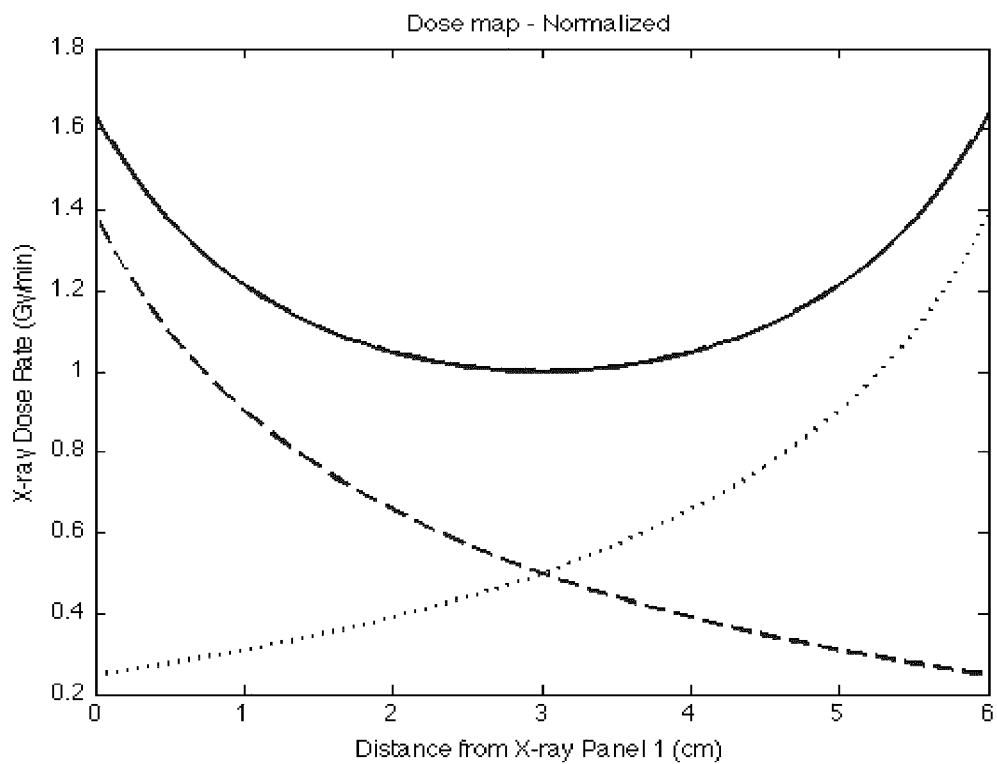
FIGS. 8A and 8B show calculated dose-depth maps of X-ray flux delivered to material in an irradiator of the present disclosure having flat panel X-ray sources placed on opposite sides of the material.
Figure 8B:
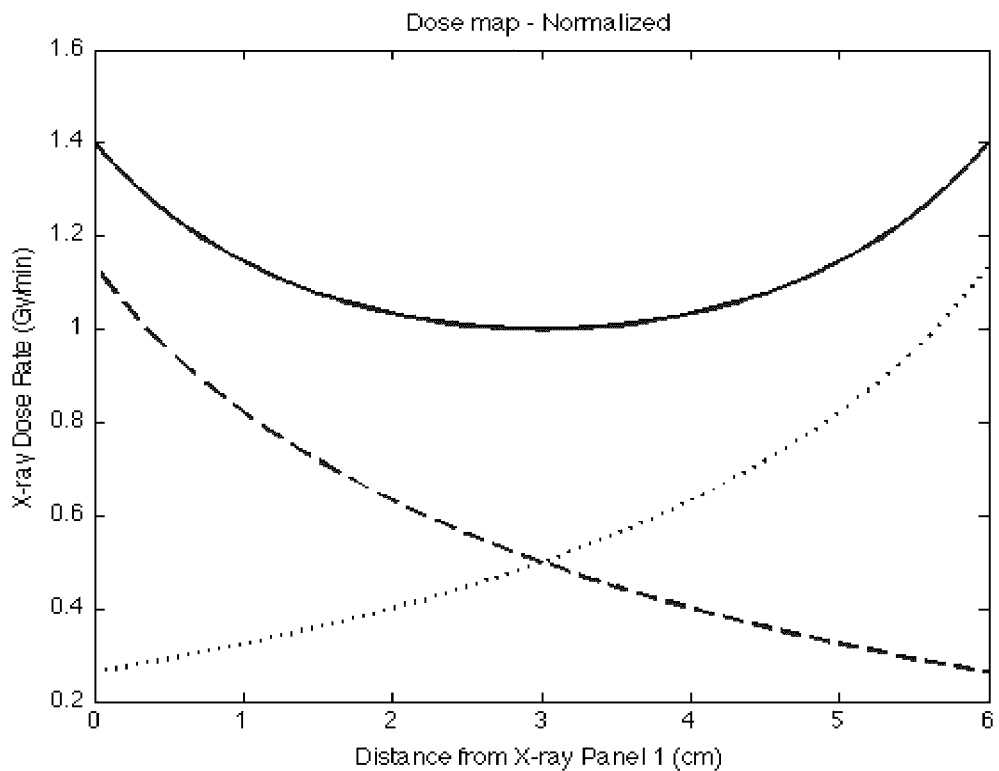

FIG. 8 shows calculated dose-depth maps of X-ray flux delivered to material in an irradiator of the present disclosure having flat panel X-ray sources placed on opposite sides of the material. In this case, the material to be irradiated is blood contained in blood bags. The normalized X-ray dose rate in Gy/min is plotted as a function of the distance from the X-ray sources. The dashed lines show the dose rate as a function of the distance from one X-ray source and the dotted lines show the dose rate as a function of the distance from the other X-ray source. The solid lines are the combined dose rate from both sources as a function of the distance. The plots are shown for 100 kV and 150 kV operating voltage. As shown in FIG. 8, dose uniformity is substantially improved by irradiating the material from opposite sides.

It will be appreciated from FIG. 5 that if all the cathodes in the cathode array of source 2 were evenly distributed over the source exit window and all operated at the same current level, the X-ray flux would be highest from the middle of the source, owing to the greater overlap of X-ray flux generation sites at the center of anode 30 as compared to the sides. Further embodiments of the disclosure provide for even flux distribution across the panel.

Figure 9:
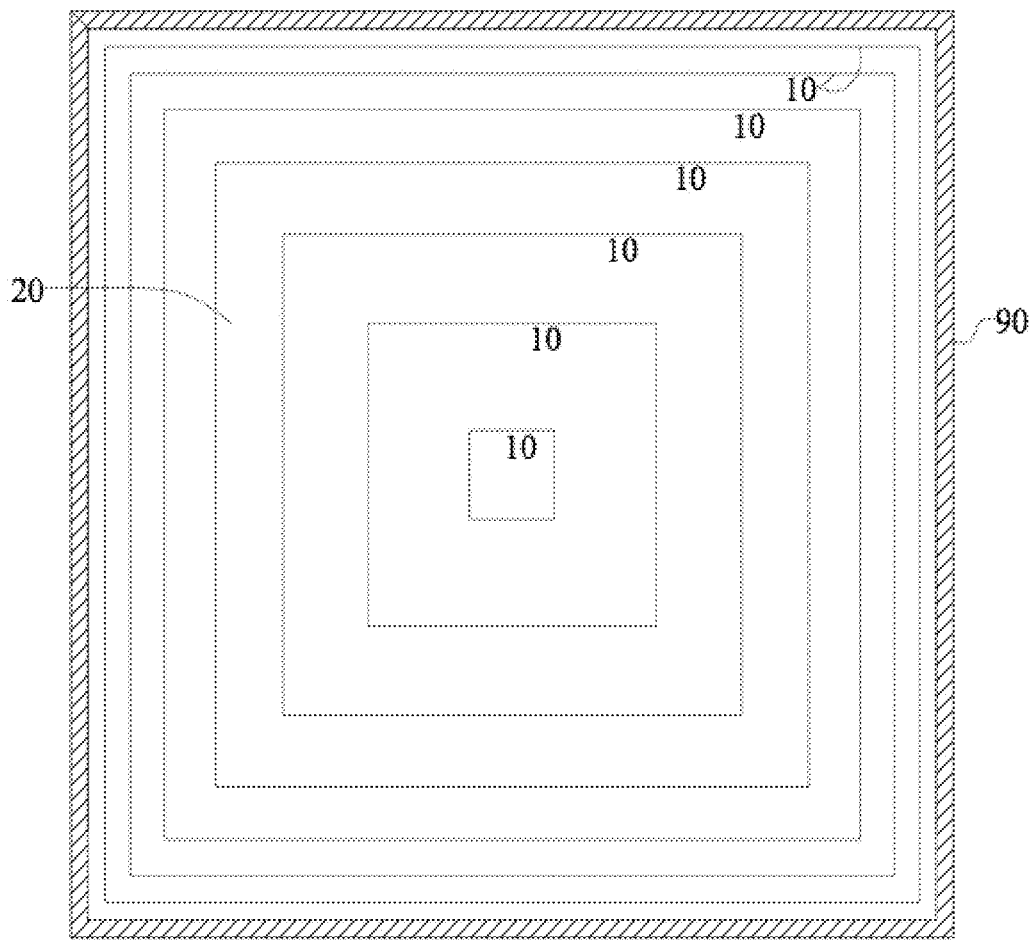
FIG. 9 shows an embodiment of the present disclosure in which the cathodes in the array of a flat panel X-ray source are made more dense towards the edges of the array away from the center, thereby smoothing out the flux distribution of the source across its emitting area.

FIG. 9 shows an embodiment of the present disclosure in which the cathodes in the array of a flat panel X-ray source are made denser towards the edges of the array away from the center, thereby smoothing out the flux distribution of the source across its emitting area. Here, the cathodes on array 100 on window 20 are made denser towards the edges of the array near source walls 90 and sparser towards the center. This provides for a corresponding change in the density of X-ray flux generation on the anode. In the case of thermal filament cathodes, the filaments are spaced closer together closer to the edge of the array. In the case of cold cathodes, the areal density the individual emitters can be increased closer to the edge of the array. For example, a cold cathode array used in a flat panel X-ray source for a blood irradiator might have an average of 24,000 individual cathodes per square centimeter, but the density of the cathode at the center of the array could be only 5,000/cm$^2$, while the density at the edges of the array could be over 50,000/cm$^2$. In another embodiment of the disclosure, the cathodes in the array may be supplied with increasingly higher current as they get closer to the edge of the array.

Figure 10:
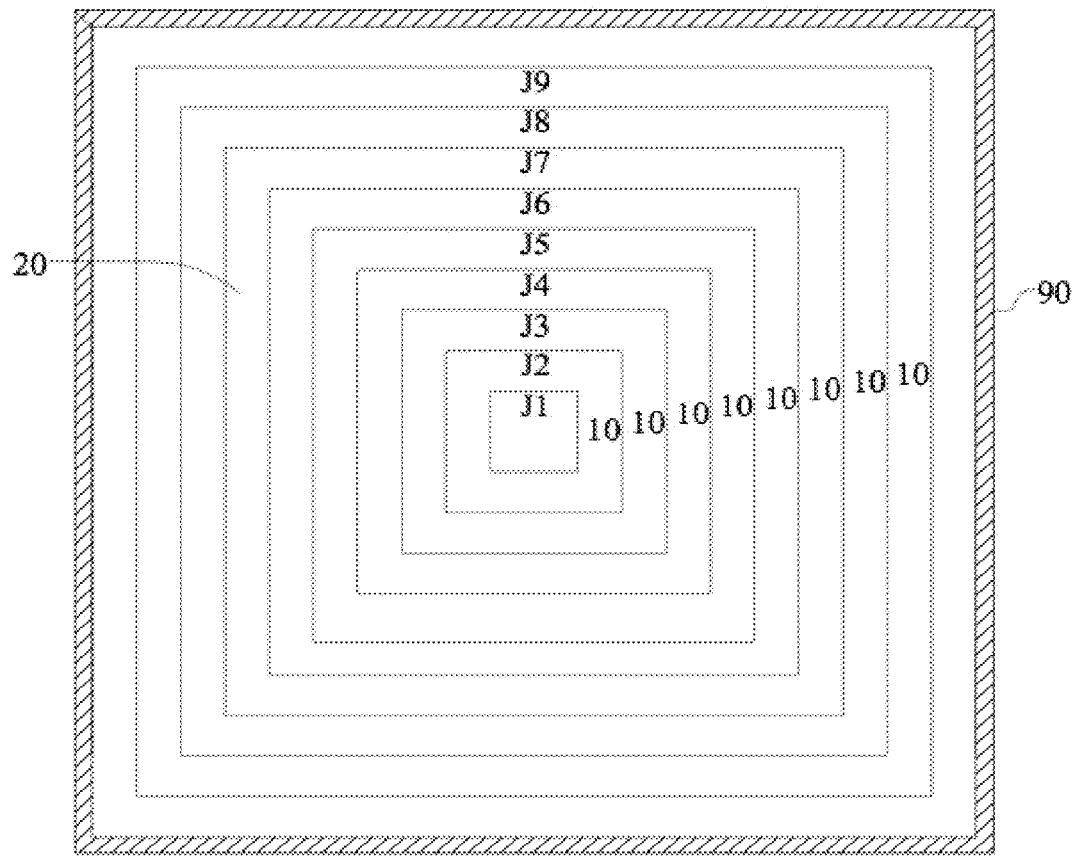
FIG. 10 shows an embodiment of the present disclosure in which the cathodes of the array in a flat panel X-ray source are supplied with greater current the further the cathodes are away from the center of the array and towards the edges of the array, thereby smoothing out the flux distribution of the source across its emitting area.
Figure 11:
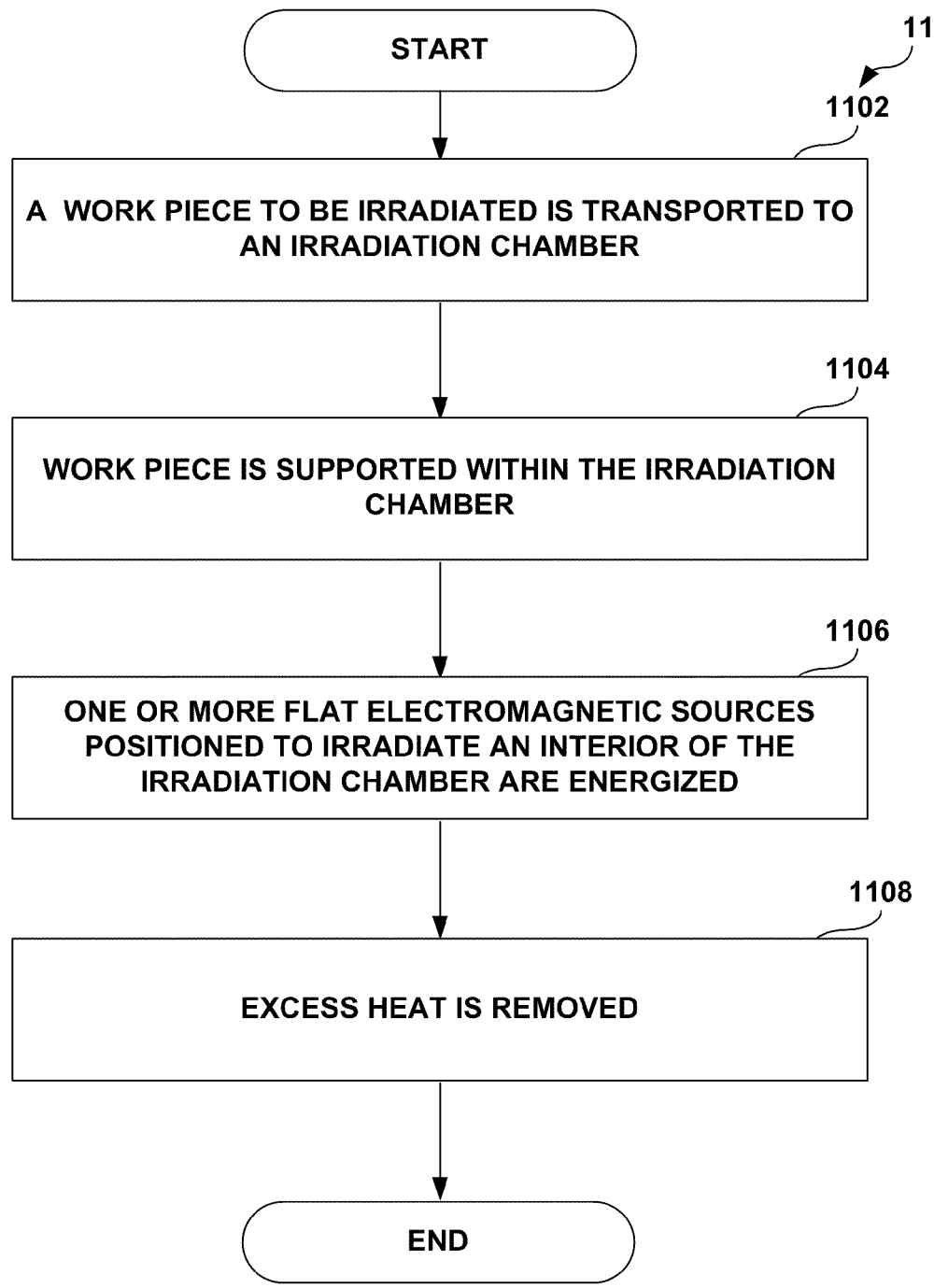
FIG. 11 provides a logic flow diagram of a method of irradiating materials in accordance with embodiments of the present disclosure

FIG. 10 shows an embodiment of the present disclosure in which the cathodes of the array in a flat panel X-ray source are supplied with greater current the further the cathodes are away from the center of the array and towards the edges of the array, thereby smoothing out the flux distribution of the source across its emitting area. J1-J9 indicate increasingly higher current levels, these increasing levels can be done with an array of evenly dense emitters, in addition to the array shown in FIG. 9 where the density is higher towards the edges of the array. In the case of a cold cathode array, for example, an exemplary setting for a general purpose irradiator of the present disclosure, including an irradiator used for high throughput blood irradiation, would be 18 mA from each of two 30 cm×30 cm square flat panel X-ray sources, for an average of 0.02 mA/cm$^2$ current density. To provide for uniform X-ray flux density across the panel, the current supplied to the cathodes at the center of the cathode array could be on the order of 0.015 mA/cm$^2$ while the current supplied to the cathodes at the edges of the array towards wall 90 could be on the order of 0.025 mA/cm$^2$. In a tiled flat panel X-ray source configuration, such as that shown in FIG. 7, but with more than four panels, variable cathode density or current density can be supplied to different panels, to smooth out X-ray flux density from the entire flux generation surface of the panels FIG. 11 provides a logic flow diagram of a method of irradiating materials in accordance with embodiments of the present disclosure. Operations 1100 begin with block 1102 where a work piece to be irradiated is transported to an irradiation chamber. This may involve placing materials directing within a chamber through a shielded portal that allows access as discussed above. A carousel within the irradiation chamber may be used to rotate the work piece within the irradiation chamber for uniform distribution of the electromagnetic flux to the work piece. In block 1104, the work piece is supported within the irradiation chamber with a low attenuation support mechanism. Then, in block 1106, one or more flat electromagnetic sources positioned to irradiate an interior of the irradiation chamber are energized at a controlled energy level and time. Excess heat is removed from the one or more flat electromagnetic source with a heat transfer system in Block 1108. The exterior is shielded from the electromagnetic flux within the irradiation chamber by a shielding system. The electromagnetic flux comprising an X-ray flux or an ultraviolet flux. A process controller may be used to coordinates the operation of the irradiation chamber; one or more flat electromagnetic sources, the heat transfer system; and the interlock system.

In summary, the present disclosure provides an apparatus and method for the X-ray irradiation of materials. This apparatus includes an irradiation chamber, a number of flat electromagnetic (X-ray) sources, a support mechanism, a heat transfer system, and a shielding system. A shielded portal within the shielding system allows access to an interior volume of the irradiation chamber. The shielded portal allows materials to be placed in and withdrawn from the irradiation chamber. When closed, the shielded portal allows a continuous shielded boundary of the interior volume of the irradiation chamber. The electromagnetic sources are positioned on or embedded with interior surfaces of the irradiation chamber. These electromagnetic sources may generate an electromagnetic flux, such as an X-ray flux, where this flux is used to irradiate the interior volume of the irradiation chamber and any materials placed therein. The materials placed within the interior of the chamber may be supported by a low attenuation support mechanism. This low attenuation support mechanism does not substantially reduce the X-ray flux intended to irradiate the materials placed within the interior volume of the irradiation chamber. Additionally the irradiation chamber may have a heat transfer system thermally coupled to the irradiation chamber and electromagnetic sources in order to remove heat from the interior surfaces of the irradiation chamber. The shielding system external to the irradiation chamber prevents unwanted radiation from escaping from within the irradiation chamber.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A self-contained irradiator comprising:
    a radiation-shielded enclosure;
    at least one flat panel X-ray source within said radiation-shielded enclosure, said at least one flat panel X-ray source operable to emit an X-ray flux across an area substantially equal to a proximate facing surface area of material placed inside said enclosure to be irradiated, each of said at least one flat panel X-ray sources comprising:
        a cathode array formed by a plurality of cathodes on a flux exit window of said source; and
        a wide, flat metallic X-ray target disposed opposite said cathode array, said wide, flat metallic X-ray target having a thickness greater than 1 mm, said wide, flat metallic X-ray target further comprising:
            a first major surface facing said cathode array and exposed to a vacuum of said source; and
            a second major surface exposed to an exterior of said source, the exit window and said X-ray target being integral major parts of a vacuum enclosure of said source; and
    wherein said cathode array is operable to emit multiple electron beams toward said X-ray target to generate the X-ray flux, a portion of the X-ray flux thereby emitted in a direction of said cathode array, passing by or through said cathodes in said array and out the exit window.

2. The irradiator of claim 1, wherein the cathode array of each of the at least one flat panel X-ray source comprises a cold cathode array with open space between individual cathodes in the array.

3. The irradiator of claim 1, wherein the cathode array of each of the at least one flat panel X-ray source comprises a thermal filament array with open space between the filaments.

4. The irradiator of claim 1, wherein the material to be irradiated comprises blood or blood products.

5. The irradiator of claim 1, wherein a density of the cathodes in the cathode array of the at least one flat panel X-ray source is varied to provide a substantially even distribution of X-ray flux from the target.

6. The irradiator of claim 1, wherein an electrical current supplied to the cathodes in the cathode array of the flat panel X-ray source is varied to provide a substantially even distribution of the X-ray flux from the target.

7. The irradiator of claim 1, further comprising a shielded portal to allow access to said radiation-shielded enclosure.

8. The irradiator of claim 7, further comprising an interlock system coupled to said shielded portal and said at least one flat panel X-ray source, said interlock system operable to prevent irradiation of said radiation-shielded enclosure when said shielded portal is open.

9. The irradiator of claim 8, further comprising a process controller operable to coordinate the operation of:
    said radiation-shielded enclosure;
    said at least one flat panel X-ray source;
    a heat transfer system operable to remove heat from said at least one flat panel X-ray source; and
    said interlock system.

10. The irradiator of claim 1, wherein a carousel within the radiation-shielded enclosure rotates a work piece to be irradiated within the radiation-shielded enclosure for uniform distribution of the X-ray flux to the work piece.

11. The irradiator of claim 1, wherein said at least one flat panel X-ray source comprises a plurality of flat panel X-ray sources.

12. The irradiator of claim 11, wherein said plurality of flat panel X-ray sources are disposed on opposite sides of said radiation-shielded enclosure.

13. The irradiator of claim 11, wherein said plurality of flat panel X-ray sources are tiled together on a side of said radiation-shielded enclosure.

14. The irradiator of claim 11, wherein said plurality of flat panel X-ray sources are tiled to irradiate the radiation-shielded enclosure, said plurality of flat panel X-ray sources operating either individually or simultaneously.

* * * * *